United States Patent [19]

Ashjian

[11] Patent Number: 5,384,055
[45] Date of Patent: Jan. 24, 1995

[54] LUBRICANT ADDITIVES

[75] Inventor: Henry Ashjian, E. Brunswick, N.J.

[73] Assignee: Mobil Oil Corporation, Fairfax, Va.

[21] Appl. No.: 977,726

[22] Filed: Nov. 16, 1992

Related U.S. Application Data

[63] Continuation of Ser. No. 866,945, Apr. 6, 1992, abandoned, which is a continuation of Ser. No. 342,179, Apr. 25, 1989, abandoned.

[51] Int. Cl.$^6$ ................. C10M 133/16; C10M 133/56
[52] U.S. Cl. ..................... 252/51.5 A; 548/545; 548/546; 548/547
[58] Field of Search .............. 252/56 R, 51.5 A; 548/545, 546, 547

[56] References Cited

U.S. PATENT DOCUMENTS

| | | | |
|---|---|---|---|
| 3,223,495 | 12/1965 | Calvino et al. | 44/347 |
| 3,590,076 | 6/1971 | Heintzelman et al. | 549/233 |
| 3,810,913 | 5/1974 | Relles | 548/548 |
| 4,158,664 | 6/1979 | Selwitz et al. | 562/593 |
| 4,203,730 | 5/1980 | Hanson | 548/548 |
| 4,396,774 | 8/1983 | Schaffhausen | 549/255 |
| 4,486,573 | 12/1984 | Hayashi | 525/285 |
| 4,526,950 | 7/1985 | Grava | 526/272 |
| 4,581,464 | 4/1986 | Ross et al. | 549/255 |
| 4,588,786 | 5/1986 | Kadono et al. | 548/548 |
| 4,599,430 | 7/1986 | Milberger et al. | 548/548 |
| 4,827,064 | 5/1989 | Wu | 585/10 |
| 4,827,073 | 5/1989 | Wu | 585/530 |

FOREIGN PATENT DOCUMENTS

| | | | |
|---|---|---|---|
| 0117784 | 5/1984 | European Pat. Off. | |
| 0455142 | 12/1975 | U.S.S.R. | 252/51.5 A |

*Primary Examiner*—Margaret Medley
*Attorney, Agent, or Firm*—A. J. McKillop; M. D. Keen

[57] ABSTRACT

A lubricant additive composition and method for production is disclosed comprising the adduct of an olefinic oligomer and an enophile, said olefinic oligomer comprising the product of the oligomerization of $C_2$ to $C_{24}$ alpha-olefin feedstock, or mixtures thereof, under oligomerization conditions in contact with a reduced valence state Group VIB metal catalyst on porous support. Maleic anhydride is a preferred enophile. The maleic anhydride adduct is reacted with polyamines such as tetraethylene pentamine to form the corresponding alkenyl bis-succinimide.

11 Claims, No Drawings

LUBRICANT ADDITIVES

CROSS REFERENCE TO RELATED APPLICATIONS

This application is a continuation of prior application Ser. No. 07/866,945, filed Apr. 6, 1992, now abandoned, which was a continuation of prior application Ser. No. 07/342,179, filed Apr. 25, 1989, now abandoned.

This invention relates to novel compositions useful as lubricant additives having polar functional groups. In particular, the invention relates to novel lubricant additive compositions and methods for their preparation from unique synthetic hydrocarbon lubricants that exhibit a high viscosity index.

BACKGROUND OF THE INVENTION

The formulation of lubricants typically includes an additive package incorporating a variety of chemicals to improve or protect lubricant properties in application specific situations, particularly internal combustion engine and machinery applications. The more commonly used additives include oxidation inhibitors, rust inhibitors, antiwear agents, pour point depressants, detergent-dispersants, viscosity index (VI) improvers, foam inhibitors and the like. This aspect of the lubricant arts is specifically described in Kirk-Othmer "Encyclopedia of Chemical Technology", 3rd edition, Vol. 14, pp477-526, incorporated herein by reference. Considering the diversity of chemical structures represented by the plethora of additives incorporated in a typical lubricant formulation, and the quantity in which they are added, the artisan in the lubricant formulation arts faces a substantial challenge to provide a homogeneous formulation which will remain stable or in solution during inventory and during use. Lubricants, particularly synthetic lubricants of the type of interest in the instant invention, are usually hydrogenated olefins. Due to their hydrocarbon structure they are largely incompatible with polar additives such as antioxidants, antirust and antiwear agents, etc. Accordingly, in order to render the lubricants compatible with the polar additives large amounts of expensive polar organic esters must be added to the formulation. Useful commercial formulations may contain 20% percent or more of such esters as bis-tridecanol adipate for example, solely to provide a fully homogeneous lubricant blend of lubricant and additive.

Modifying the solvent properties of lubricants with solubilizing agents such as organic esters, while solving the problem of how to prepare stable blends with lubricant additives, creates or accentuates other performance related problems beyond the added burden on cost of the product. The vulnerability of solubilizing agents to oxidative degradation promoting the formation of tars and gums must be taken into account. Seal swelling properties may be changed. Seal swell measures the ability of a lubricant to swell a seal, thus enhancing its sealing function. Solubilizing agents may effect viscometric properties such as viscosity and viscosity index of the material. When materials deficient in these properties are added in large amounts, the lubricant's effectiveness will be impaired. In view of these complications it is evident that novel approaches are called for in the modification or formulation of lubricants to incorporate additives without compromising properties or adding significantly to the cost of the product.

One approach to improve lubricant compatibility with additives is to add polar groups to the structure of the lubricant. Lubricants, in particular synthetic lubricants, are known to contain olefinic unsaturation and it has been determined in the present invention that such unsaturation can be effectively utilized to react with polar groups to add a polar functionality on to the lubricant molecule. The added polar group in the lubricant has sufficient solubilizing character to adequately dissolve additive packages without the addition of solubilizing agents such as adipate esters. It has been discovered in the instant invention that the necessary functionality i.e., functional group, can be added to the lubricant by reacting the lubricant olefinic group with an electronegative enophile. Depending upon the structure of the molecule added to the olefin unsaturation of the lubricant other property improvements typical of additive packages may also be conferred upon the lubricant mixture.

Recently, novel lubricant compositions (referred to herein as HVI-PAO and the HVI-PAO process) comprising polyalpha-olefins and methods for their preparation employing as catalyst reduced chromium on a silica support have been disclosed in U.S. patent applications Ser. Nos. 210,434 and 210,435, now U.S. Pat. Nos. 4,827,073 and 4,827,064 filed Jun. 23, 1988, incorporated herein by reference in their entirety. The process comprises contacting $C_6$-$C_{20}$ 1-alkene feedstock with reduced valence state chromium oxide catalyst on porous silica support under oligomerizing conditions in an oligomerization zone whereby high viscosity, high viscosity index (VI) liquid hydrocarbon lubricant is produced having branch ratios, i.e. $CH_3/CH_2$, less than 0.19 and pour point below $-15°$ C. The process is distinctive in that little isomerization of the olefinic bond occurs compared to known oligomerization methods to produce polyalpha-olefins using Lewis acid catalyst. Lubricants produced by the process cover the full range of lubricant viscosities and exhibit a remarkably high viscosity index (VI) and low pour point even at high viscosity. The assynthesized HVI-PAO oligomer has a preponderance of terminal olefinic unsaturation or exo-olefinic groups, e.g., vinylidene groups.

It is an object of the present invention to provide novel derivatives of HVI-PAO oligomers containing polar functional groups suitable as lubricant additives.

Another object of the present invention is to provide methods for the production of HVI-PAO lubricants containing polar functional groups that provide superior additive properties.

Yet another object of the present invention is to incorporate polar groups in HVI-PAO lubricants by addition of electronegative groups to lubricant olefinic unsaturation.

SUMMARY OF THE INVENTION

It has been discovered that unsaturated $C_{20}+$ HVI-PAO lubricant range hydrocarbons containing an allylic hydrogen will react thermally or catalytically by addition to an alkene which contains olefinic unsaturation in the alpha,beta position to an electronegative group when the $C_{20}+$ HVI-PAO unsaturated lubricant has the following structure comprising one or more allylic hydrogens:

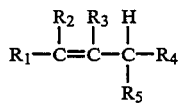

where $R_1$, $R_2$, $R_3$, $R_4$ and $R_5$ may be hydrogen, alkyl or alkenyl and at least 17 carbon atoms in total. In a preferred embodiment $R_1$ and $R_2$ are hydrogen and the unsaturated olefin is a vinlyidene group comprising a terminal group of the HVI-PAO hydrocarbon molecule.

The alpha, beta unsaturated alkenes useful in the present invention include all those having the structure:

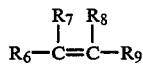

where at least one of $R_6$, $R_7$, $R_8$ and $R_9$ is an electronegative negative group and the remainder hydrogen, alkyl, alkenyl, alkynalkyl, aryl or aralkyl. These structures are referred to herein, as in the organic chemical arts, as enophiles. Maleic anhydride is a preferred enophile.

More particularly, a polar lubricant composition has been discovered comprising the adduct of the above unsaturated lubricant and unsaturated alkene and having the structure:

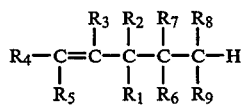

where at least one of $R_8$ or $R_9$ is an electronegative group and the remainder $R_6$, $R_7$, $R_8$ and $R_9$ is an electronegative group or hydrogen, alkyl, alkenyl, alkynalkyl, aryl or aralkyl and $R_1$, $R_2$, $R_3$, $R_4$ and $R_5$ is hydrogen, alkyl or alkenyl at least one of which is $C_{17}+$ alkyl or alkenyl group. Where the unsaturated $C_{20}+$ HVI-PAO lubricant molecule contains multiple allylic groups more than one mole of enophile can react with the lubricant to form an adduct containing more than one electronegative group or multiple polar sites.

Typically, the product of the invention containing olefinic unsaturation exhibits useful properties for additive applications and can be used as an additive without further change. However, hydrogenation of the olefinic bonds of the adduct yields a polar product also with useful properties for additives applications, e.g., dispersant properties.

The HVI-PAO unsaturated lubricant employed in the present invention comprises a liquid lubricant hydrocarbon composition comprising the polymeric residue of 1-alkenes taken from the group consisting essentially of linear $C_6$-$C_{20}$ 1-alkenes, said composition having a branch ratio of less than 0.19, weight average molecular weight between 300 and 45,000, number average molecular weight between 300 and 18,000, molecular weight distribution between 1 and 5 and pour point below $-15°$ C.

The formation of the HVI-PAO adduct between $C_{20}+$ olefinic lubricant and an enophile is accomplished in the present invention by heating the mixture at elevated temperature or by reaction catalyzed by a Lewis acid such as $BF_3$ or $AlCl_3$.

DETAIL DESCRIPTION OF THE INVENTION

The olefinic lubricants useful in the present invention in the formation of adducts with enophiles include all those unsaturated HVI-PAO lubricants having 20 to 5000 carbon atoms where one or more of the unsaturated groups is allylic unsaturation. To be useful in the present invention all such lubricant molecules must contain one or more olefinic group of the following structure:

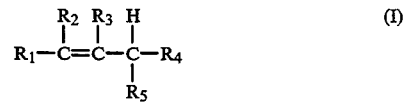

where $R_1$, $R_2$, $R_3$, $R_4$ and $R_5$ may be hydrogen, alkyl or alkenyl and at least 17 carbon atoms in total for the sum of carbon atoms in $R_1$, $R_2$, $R_3$, $R_4$ and $R_5$. The olefinic bond may be in the alpha position, i.e., a vinyl structure where $R_1$ and $R_2$ are hydrogen, or the bond may be an internal olefin where $R_1$, $R_2$, $R_3$, $R_4$ and/or $R_5$ is an aliphatic hydrocarbon. Preferable the olefinic group comprises a vinylidene group of the structure $CH_2=CR_2$ where R is the HVI-PAO moiety. Since lubricants comprise a mixture of molecules usually having a wide range of molecular weights certain molecules may contain more than one olefinic bond, including alpha olefins and internal olefins of allylic structures. It is to be expected then that certain lubricant molecules may be produced according to this invention containing multiple adducts with specific enophiles, following reaction at multiple olefinic sites in the unsaturated lubricant molecule. As oligomerized, HVI-PAO oligomers are mixtures of dialkyl vinylidenic and 1,2 dialkyl or trialkyl mono-olefins. In general, the novel HVI-PAO oligomers have the following regular head-to-tail structure where n can be 3 to 17:

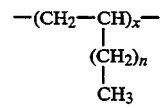

with some head-to-head connections.

It has been found that the process described herein to produce the HVI-PAO oligomers used in the present invention can be controlled to yield oligomers having weight average molecular weight between 300 and 45,000 and number average molecular weight between 300 and 18,000. Measured in carbon numbers, molecular weights range from $C_{30}$ to $C_{1300}$ and viscosity up to 750 cs at 100° C., with a preferred range of $C_{30}$ to $C_{1000}$ and a viscosity of up to 500 cs at 100° C. Molecular weight distributions (MWD), defined as the ratio of weight average molecular to number average molecular weight, range from 1.00 to 5, with a preferred range of 1.01 to 3 and a more preferred MWD of about 1.05 to 2.5.

Olefins suitable for use as starting material to prepare unsaturted HVI-PAO oligomers for this invention include those olefins containing from 2 to about 24 carbon atoms such as ethylene, propylene, 1-butene, 1-pentene, 1-hexene, 1-octene, 1-decene, 1-dodecene and 1-tetradecene and branched chain isomers such as 4-methyl-1- pentene. Also suitable for use are olefin-containing refinery feedstocks or effluents. However, the olefins used are preferably alpha-olefinic olefinic as for example 1-heptene to 1-hexadecene and more preferably 1-octene to 1-tetradecene, or mixtures of such olefins.

HVI-PAO oligomers of alpha-olefins have a low branch ratio of less than 0.19 and superior lubricating properties compared to the alpha-olefin oligomers with a high branch ratio, as produced in all known commercial methods.

HVI-PAO oligomers are prepared by oligomerization reactions in which a major proportion of the double bonds of the alphaolefins are not isomerized. These reactions include alpha-olefin oligomerization by supported metal oxide catalysts, such as Cr compounds on silica or other supported IUPAC Periodic Table Group VIB compounds. The catalyst most preferred is a lower valence Group VIB metal oxide on an inert support. Preferred supports include silica, alumina, titania, silica alumina, magnesia and the like. The support material binds the metal oxide catalyst. Those porous substrates having a pore opening of at least 40 angstroms are preferred.

The support material usually has high surface area and large pore volumes with average pore size of 40 to about 350 angstroms. The high surface area is beneficial for supporting large amounts of highly dispersive, active chromium metal centers and to give maximum efficiency of metal usage, resulting in very high activity catalyst. The support should have large average pore openings of at least 40 angstroms, with an average pore opening of >60 to 300 angstroms preferred. This large pore opening will not impose any diffusional restriction of the reactant and product to and away from the active catalytic metal centers, thus further optimizing the catalyst productivity. Also, for this catalyst to be used in fixed bed or slurry reactor and to be recycled and regenerated many times, a silica support with good physical strength is preferred to prevent catalyst particle attrition or disintegration during handling or reaction.

The supported metal oxide catalysts are preferably prepared by impregnating metal salts in water or organic solvents onto the support. Any suitable organic solvent known to the art may be used, for example, ethanol, methanol, or acetic acid. The solid catalyst precursor is then dried and calcined at 200° to 900° C. by air or other oxygen-containing gas. Thereafter the catalyst is reduced by any of several various and well known reducing agents such as, for example, CO, $H_2$, $NH_3$, $H_2S$, $CS_2$, $CH_3SCH_3$, $CH_3SSCH_3$, metal alkyl containing compounds such as $R_3Al$, $R_3B, R_2Mg$, RLi, $R_2Zn$, where R is alkyl, alkoxy, aryl and the like. Preferred are CO or $H_2$ or metal alkyl containing compounds. Alternatively, the Group VIB metal may be applied to the substrate in reduced form, such as CrII compounds. The resultant catalyst is very active for oligomerizing olefins at a temperature range from below room temperature to about 250° C. at a pressure of 0.1 atmosphere to 5000 psi. Contact time of both the olefin and the catalyst can vary from one second to 24 hours. The catalyst can be used in a batch type reactor or in a fixed bed, continuous-flow reactor.

In general the support material may be added to a solution of the metal compounds, e.g., acetates or nitrates, etc., and the mixture is then mixed and dried at room temperature. The dry solid gel is purged at successively higher temperatures to about 600° for a period of about 16 to 20 hours. Thereafter the catalyst is cooled down under an inert atmosphere to a temperature of about 250° to 450° C. and a stream of pure reducing agent is contacted therewith for a period when enough CO has passed through to reduce the catalyst as indicated by a distinct color change from bright orange to pale blue. Typically, the catalyst is treated with an amount of CO equivalent to a two-fold stoichiometric excess to reduce the catalyst to a lower valence CrII state. Finally the catalyst is cooled down to room temperature and is ready for use.

The product oligomers have a very wide range of viscosities with high viscosity indices suitable for high performance lubrication use. The product oligomers also have atactic molecular structure of mostly uniform head-to-tail connections with some head-to-head type connections in the structure. These low branch ratio oligomers have high viscosity indices at least about 15 to 20 units and typically 30–40 units higher than equivalent viscosity prior art oligomers, which regularly have higher branch ratios and correspondingly lower viscosity indices. These low branch oligomers maintain better or comparable pour points.

The branch ratios defined as the ratios of $CH_3$ groups to $CH_2$ groups in the lube oil are calculated from the weight fractions of methyl groups obtained by infrared methods, published in *Analytical Chemistry*, Vol. 25, No. 10, p. 1466 (1953).

$$\text{Branch ratio} = \frac{\text{wt fraction of methyl group}}{1 - (\text{wt fraction of methyl group})}$$

To produce the HVI-PAO low molecular weight products suitable for use in the present invention the reaction is carried out at a temperature of 90°–250° C.

The following examples are presented for illustration of the preparation of HVI-PAO unsaturated oligomers used in the instant invention.

EXAMPLE 1

Catalyst Preparation and Activation Procedure 1.9 grams of chromium (II) acetate ($Cr_2(OCOCH_3)_4 2H_2O$) (5.58 mmole) (commercially obtained) is dissolved in 50 cc of hot acetic acid. Then 50 grams of a silica gel of 8–12 mesh size, a surface area of 300 m²/g, and a pore volume of 1 cc/g, also is added. Most of the solution is absorbed by the silica gel. The final mixture is mixed for half an hour on a rotavap at room temperature and dried in an open-dish at room temperature. First, the dry solid (20 g) is purged with $N_2$ at 250° C. in a tube furnace. The furnace temperature is then raised to 400° C. for 2 hours. The temperature is then set at 600° C. with dry air purging for 16 hours. At this time the catalyst is cooled down under $N_2$ to a temperature of 300° C. Then a stream of pure CO (99.99% from Matheson) is introduced for one hour. Finally, the catalyst is cooled down to room temperature under $N_2$ and ready for use.

EXAMPLE 2

The catalyst prepared in Example 1 (3.2 g) is packed in a ⅜" stainless steel tubular reactor inside an $N_2$ blanketed dry box. The reactor under $N_2$ atmosphere is then heated to 150° C. by a single-zone Lindberg furnace. Prepurified 1-hexene is pumped into the reactor at 140 psi and 20 cc/hr. The liquid effluent is collected and stripped of the unreacted starting material and the low boiling material at 0.05 mm Hg. The residual clear, colorless liquid has viscosities and VI's suitable as a lubricant base stock.

| Sample | Prerun | 1 | 2 | 3 |
|---|---|---|---|---|
| T.O.S., hr. | 2 | 3.5 | 5.5 | 21.5 |
| Lube Yield, wt % | 10 | 41 | 74 | 31 |
| Viscosity, cS, at | | | | |
| 40° C. | 208.5 | 123.3 | 104.4 | 166.2 |
| 100° C. | 26.1 | 17.1 | 14.5 | 20.4 |
| VI | 159 | 151 | 142 | 143 |

EXAMPLE 3

Similar to Example 2, a fresh catalyst sample is charged into the reactor and 1-hexene is pumped to the reactor at 1 atm and 10 cc per hour. As shown below, a lube of high viscosities and high VI's is obtained. These runs show that at different reaction conditions, a lube product of high viscosities can be obtained.

| Sample | A | B |
|---|---|---|
| T.O.S., hrs. | 20 | 44 |
| Temp., °C. | 100 | 50 |
| Lube Yield, % | 8.2 | 8.0 |
| Viscosities, cS at | | |
| 40° C. | 13170 | 19011 |
| 100° C. | 620 | 1048 |
| VI | 217 | 263 |

EXAMPLE 4

A commercial chrome/silica catalyst which contains 1% Cr on a large-pore volume synthetic silica gel is used. The catalyst is first calcined with air at 800° C. for 16 hours and reduced with CO at 300° C. for 1.5 hours. Then 3.5 g of the catalyst is packed into a tubular reactor and heated to 100° C. under the $N_2$ atmosphere. 1-Hexene is pumped through at 28 cc per hour at 1 atmosphere. The products are collected and analyzed as follows:

| Sample | C | D | E | F |
|---|---|---|---|---|
| T.O.S., hrs. | 3.5 | 4.5 | 6.5 | 22.5 |
| Lube Yield, % | 73 | 64 | 59 | 21 |
| Viscosity, cS, at | | | | |
| 40° C. | 2548 | 2429 | 3315 | 9031 |
| 100° C. | 102 | 151 | 197 | 437 |
| VI | 108 | 164 | 174 | 199 |

These runs show that different Cr on a silica catalyst are also effective for oligomerizing olefins to lube products.

EXAMPLE 5

As in Example 4, purified 1-decene is pumped through the reactor at 250 to 320 psi. The product is collected periodically and stripped of light products boiling points below 650° F. High quality lubes with high VI are obtained (see following table).

| Reaction Temp. °C. | WHSV g/g/hr | Lube Product Properties | | |
|---|---|---|---|---|
| | | V at 40° C. | V at 100° C. | VI |
| 120 | 2.5 | 1555.4 cs | 157.6 cs | 217 |
| 135 | 0.6 | 389.4 | 53.0 | 202 |
| 150 | 1.2 | 266.8 | 36.2 | 185 |
| 166 | 0.6 | 67.7 | 12.3 | 181 |
| 197 | 0.5 | 21.6 | 5.1 | 172 |

The enophiles useful in the present invention include all those having the structure:

$$\begin{array}{c} R_7 \ R_8 \\ | \ \ | \\ R_6-C=C-R_9 \end{array} \quad (II)$$

where at least one of $R_6$, $R_7$, $R_8$ and $R_9$ is an electronegative group and the remaining groups are hydrogen, alkyl, alkenyl, aryl or aralkyl. The electronegative groups useful in the enophiles of structure (II) include:

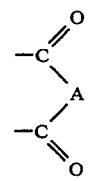

where A is O, NH, NR where R is alkyl or alkenyl;

where Z is H, OH, $NH_2$, halogen, alkyl, aryl, benzyl; and groups such as $-CN$, $-NO_2$, aryl, benzyl, $-CH_2CN$, $-CH_2X$ where X is halogen,

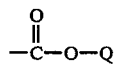

where Q is alkyl, aryl or benzyl. Enophiles of particular use in the instant invention include maleic anhydride, maleimide, acrylonitrile, styrene, 4-carboethoxy styrene, ethylacrylate, acrylamide, acrolein, methyl vinyl ketone, phenyl vinyl ketone, cinnamyl chloride, 4-sulfamyl styrene, methacrylic acid, ethyl vinyl carbonate, 2-hydroxyethyl acryate and the like.

The novel lubricants of the present invention are prepared according to the well-known "Ene" reaction by reacting the unsaturated lubricants and enophiles described above thermally or in contact with catalyst to form the unsaturated adduct. The "Ene" reaction is described in "Accounts of Chemical Research", 1980, 13, 426–432 by B. B. Snider, incorporated herein by reference in its entirety. Upon completion of the "Ene" reaction and formation of the adduct, the unsaturated adduct can be used directly as lube additive or the unsaturated adduct can be hydrogenated by means well known in the art to produce the polar lubricants of the invention. The adduct (III) and the polar saturated lubricant (IV) have the structure:

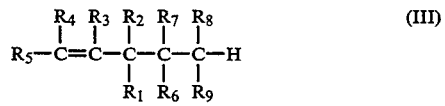

where, in (III) and (IV), $R_1$ through $R_5$ may be hydrogen, alkyl or alkenyl and the sum of carbon atoms in all $R_1$ through $R_5$ groups totals at least 17, where at least one of $R_8$, $R_9$ is an electronegative group with the remaining groups of $R_6$ through $R_9$ being an electronegative group or hydrogen, alkyl, alkenyl, alkynalkyl, aryl or aralkyl $C_1$–$C_{30}$ alkyl such as methyl, ethyl, 2-hydroxyethyl, propyl, octyl, lauryl and the like.

The unsaturated HVI-PAO adduct with maleic anhydride, or the saturated adduct, can react with amines or polyamines such as tetraethylenepentamine (TEPA), $HN(CH_2CH_2NHCH_2CH_2NH2)_2$, to form bis-succinimides (VII):

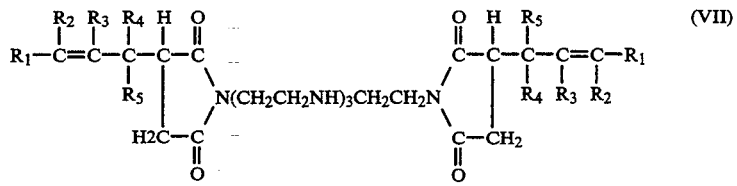

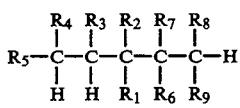

Where the unsaturated lubricant feedstock contains molecules having muliple sites of allylic unsaturation, the Ene reaction will produce an adduct containing multiple enophile moieties comprising lubricant molecules of particularly enhanced polarity.

As noted above, the Ene reaction adduct formation between unsaturated lubricant molecules and enophiles may be conducted thermally at temperatures between 100° C. and 400° C. either neat or in a solvent. The process may be conducted as a batch process or continuous. Where catalysts are used, Lewis acid catalysts are preferred such as $BF_3$, $AlCl_3$, $(CH_3)_2AlCl$, $SnCl_4$, $C_2H_5AlCl_2$ and the like.

The scope of the present invention includes the further reaction of the polar function of the hydrogenated or unsaturated adducts prepared by the process of the invention to provide further useful products, typically enhancing the properties of the lubricant. For example, the nitrile function of adducts prepared from acrylonitrile may be hydrolyzed to acid or amide or esterified by methods well known in the art. Hydrogenation of the adduct formed between an unsaturated HVI-PAO lubricant and maleic anhydride produces the substituted succinic anhydride which may be further reacted with alcohol by known means to yield a diester of the structure (V) from the anhydride (VI):

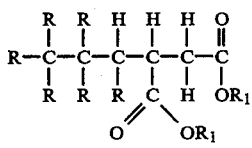

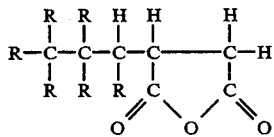

where R in (V) and (VI) is hydrogen, alkyl or alkenyl and the total number of carbon atoms in all R groups is at least 17 and, preferably, with at least one R group a lubricant moiety of between $C_{17}$ and $C_{1000}$ carbon atoms, more preferably between $C_{30}$–$C_{60}$. $R_1$ of (V) is where $R_1$, $R_2$, $R_3$, $R_4$, and $R_5$ are hydrogen, alkyl, or alkenyl and at least 17 carbon atoms in total.

In the following examples the process and products of the instant invention are described together with the distinguishing characteristics of the novel products.

EXAMPLE 6

2400 grams (2.20 moles) of HVI-PAO polydecene prepared as described herein before having a bromine number of 14.6 and a calculated molecular weight of 1090 is reacted at 254° C. with 235 grams (2.40 moles) of maleic anhydride for six hours. The batch after six hours is vacuum stripped at 175° C. and 10 mm to remove unreacted maleic anhydride. The yield after stripping is 2612 grams the acid number run under anhydride conditions is 44.8. Theoretical acid value for a molecular adduction of polydecene and maleic anhydride is 47.2. Therefore, conversion is 95% to anhydride adduct. The adduct prepared from HVI-PAO polydecene was "char free" with no evidence of tarry deposits on the reactor walls.

EXAMPLE 7

3000 grams (2.80 moles) of HVI-PAO polydecene with a bromine number of 14.87 and a calculated molecular weight of 1069 is reacted with 294 grams (3.0 moles) of maleic anhydride at 254° C. for eight hours. The batch is stripped at 175° C. and 10 mm pressure to remove any unreacted maleic anhydride. The yield on the stripped batch is 3275 grams and the acid number run under anhydrous conditions is 45.4. Theoretical acid number based on equi-molar is 48.0. Conversion, therefore is 94.5%. The reaction as in Example 6, was free from char or tarry deposits.

EXAMPLE 8

2000 grams (1.51 moles) of polydecene prepared using conventional Friedel-Crafts catalysis having a bromine number of 12.0 and a calculated molecular weight of 1325 is reacted with 175 grams of maleic anhydride (1.78 moles) for seven hours at 254° C. The batch is stripped free of excess maleic anhydride at 175° C. and 10 mm pressure. Product yield is 2119 grams, and the acid number found is 21.0 as determined by ASTM D-664 using an anhydrous solvent median. Theoretical acid number for equi-molar reaction is 39.4. Based on the 21.0 found and the low yield the conversion to anhydride is 54.3%. Considerable decomposition of maleic anhydride and polydecene occurred during adduction.

EXAMPLE 9

3035 grams (2.57 moles) of polydecene prepared using conventional catalysis with a bromine number of 13.5 and a calculated molecular weight of 11.77 is reacted at 254° C. with 266 grams (2.71 moles) of maleic anhydride for 9 hours. The batch is stripped free of excess maleic anhydride at 175° C. and 10 mm. Product yield is 3216 grams with an acid number of 24.5. Theoretical acid number which would result from an equimolar reaction of polydecene and maleic is 43.0. Accordingly, conversion is 56.0%. The reactor showed a considerable amount of tar and char deposits.

EXAMPLE 10

1150 grams (1 mole) of HVI-PAO polybutene prepared as described herein before with a bromine number of 13.8 is reacted with 118 grams (1.20 moles) of maleic anhydride at 225° C. for eight hours. The acid number of the unstripped material in the reactor after eight hours is 51.9 versus a calculated value of 53.0 indicative of very little charring or decomposition of maleic anhydride. The batch is then stripped free of unreacted maleic anhydride. The yield in the reactor is 1235 grams, the acid number is 41.0. Calculated acid number is 44.9. Accordingly, conversion is 93.3%.

EXAMPLE 11

570 grams (0,427 moles) of HVI-PAO polybutene prepared as described herein before with a bromine number of 11.9 is reacted with 50.4 grams of maleic anhydride (0.514 moles) for nine hours at 225° C. The batch is stripped free of excess maleic anhydride. The yield is 609 grams. The acid number is 36.5 versus a calculated value of 39.2. The conversion therefore is 93.0%.

EXAMPLE 12

1500 grams (1.57 moles) of a commercially available polyisobutylene prepared via Friedel-Crafts catalysis with a molecular weight of 950 is reacted with 185 grams (1.89 moles) of maleic anhydride for eight and one half hours. The acid number of the unstripped adduct is found to be 53 indicative of 15% maleic decomposition as evidenced by heavy char and tarry deposits. Upon stripping out the unreacted maleic anhydride, the acid number is found to be 40.2 versus a theoretical acid number for equi-molar reaction of 53.2. Accordingly, conversion is approximately 75%.

EXAMPLE 13

Approximately 1000 grams (0,786 moles) of alkenyl succinic anhydride (ASA) from Example 6 with a calculated combining weight of 1272 (95% ASA; 5% polydecene) is reacted with 74 grams (0.39 moles) of tetraethylene pentamine at 400° F. to make the corresponding bis-succinimide. Upon analysis of the product the percent nitrogen was 2.5, with a total base number of 52.8 (ASTM D-2896). The viscosity at 100% active at 210° F. is 106 cSt and the acid number is 0.67.

EXAMPLE 14

1000 grams (0.374 moles) of the alkenyl succinic anhydride (ASA) from Example 8 with a calculated combining weight of 2671 (54.3% ASA; 45.7% polydecene) is reacted with 35 grams (0.185 moles) of tetraethylene pentamine at 400° F. (204° C.) to make the corresponding bis-succinimide. Approximately six and one half grams of water is removed. The final product on analysis has a total base number of 23.2%, with percent nitrogen of 1.2%. The viscosity at 210° F. is 84.6 cSt. The acid number is 0.86.

From a comparison of the preceding Examples it is evident that the preparation of alkenyl succinic anhydrides using HVI-PAO oligomers to react with maleic anhydride proceeds with much higher conversion than comparable reactions using conventional oligomers prepared by oligomerization of alpha-olefins with Friedel-Crafts catalyst. Surprisingly, the reaction of the present invention also preceeds without the formation of substantial quantities of char and tarry deposits, as found in the art heretofore.

Examples 6 and 7 compare HVI-PAO polydecene oligomers of different molecular weight adducted with maleic anhydride versus polydecene prepared using conventional Friedel-Crafts catalyst as in Examples 9 and 10. Examples 11 and 12 compare HVI-PAO polybutene of different molecular weight versus a typical commercially available polyisobutylene prepared by Friedel-Crafts catalyst, as in Example 12.

In all cases the reactivity with the oligomers-polymers prepared by the HVI-PAO process is superior as shown by the amount of adducted maleic anhydride as measured by acid number and the resulting yield of anhydride in the stripped product.

The adducts prepared in these Examples can subsequently be reacted with a large variety of amines, alcohols, epoxides and combinations thereof for application in both fuel and lubes oil additives.

In Examples 13 and 14 a comparison is shown between two bis-succinimide ashless dispersants from alkenyl succinic anhydrides made from HVI-PAO oligomer, Example 13, and one from Friedel-Crafts catalysis, Example 14. The succinic adduct from the HVI-PAO decene contains 95% succinic adduct (Example 6) versus 53% for the one prepared from Friedel-Crafts catalysis (Example 9). Therefore, the resulting HVI-PAO alkyl bis-succinimide contains twice the nitrogen content. Since it is well known in the art that the percent nitrogen is related to dispersancy achievable in any one formulation containing a dispersant additive only one half as much bis-succinimide from Example 13 would be required compared to Example 14 which is the conventionally derived product.

The foregoing process for the preparation of the adduct between an HVI-PAO olefinic oligomer and an enophile can be carried out at an elevated temperature between 40 and 400° C., but preferably about 250° C. The adduct containing olefinic unsaturated can be reacted to saturate the olefin group by hydrogenating the adduct in contact with hydrogenating catalyst such as Pt or Pd and hydrogen at temperature between 20° and 300° C. whereby the olefin hydrogenated adduct of said oligomer and enophile is produced.

The surprising discovery has been made that the bis-succinimide ashless dispersants of the present invention prepared from the HVI-PAO and maleic anhydride adduct show significantly higher thermal stability than commercially available bis-succinimide prepared from polyisobutylene. A comparison of the two products is presented in Table 1 where Column A is the commercially available ashless dispersant (Amoco) and Column B is the product of the present invention. The alkenyl succinic anhydride of the present invention is prepared in substantially higher conversion (95% vs 75%) than the commercial product. Comparison of the thermal stability of the two products is made by thermogravametric analysis (TGA). That analysis shows a substantially lower weight loss for the product of the instant invention (79.83% vs 93.11%).

TABLE 1

| | Alkenyl Succinic Anhydride | |
| --- | --- | --- |
| | A | B |
| Type olefin | polyisobutylene | polydecene (HVI-PAO) |
| Source | Amoco | |
| MW | 950 | 1090 |
| % conversion | 75 | 95 |
| Bis-Succinimide | | |
| ASA/TEPA, mole ratio | 2/1 | 2/1 |
| Viscosity @210° F., cSt | 300 | 106.2 |
| TBN | 40 | 52.8 |
| % Active | 80 | 100 |
| TGA Wt. loss %, 10°/min. | | |
| 200° C. | 2.23 | 0.0 |
| 250 | 11.05 | 0.45 |
| 300 | 24.99 | 2.45 |
| 350 | 42.47 | 12.35 |
| 400 | 88.14 | 56.9 |
| 450 | 93.11 | 79.83 |

The maleic anhydride adducts of the olefin oligomers may be used for the preparation of a wide range of additives useful in lubricating oils, hydraulic fluids and other industrial fluids. The maleic anhydride adducts are especially useful for the preparation of ashless detergents and dispersants formed by reaction of the anhydride group deriving from the maleic anhydride with one or more active hydrogen-containing compounds, especially nitrogen containing compounds such as amines, organic hydroxy compounds such as phenols and alcohols, and compounds which contain more than one type of active hydrogen, for example, hydroxyamines, or which contain multiple functional groups of a similar type as in polyamines and polyols. Examples of such reaction products are disclosed in British Patent No. 1,306,529 as well as in a number of U.S. patents including those referred to in U.S. Pat. No. 4,344,854 (col. 10). Reference is made to those patents for a disclosure of exemplary reaction products of this type. The maleic anhydride adducts produced from the oligomers of the present invention can be produced in similar manner to those described in those patents except that the long chain alkenyl groups will be replaced by olefin oligomer groups produced by the present oligomerization technique. The olefin oligomers react readily with maleic anhydride using conventional techniques to form adducts which can then be reacted with other materials to form the additives.

A particularly useful class of reaction products are those produced by reaction of the maleic anhydride/olefin oligomer adduct with materials containing one or more amino groups. Those reaction products may generally be characterized as substituted succinimides (mono- and bis-succinimides) which are useful as dispersants in lubricating oils. These succinimide type compounds may be made by reaction of the maleic anhydride adducts with various amino type compounds including amines e.g. alkylamines, polyamines, substituted amines such as hydroxyamines, haloalkylamines, N-substituted aminoalkylamines and other nitrogenous compounds such as the substituted and unsubstituted piperazines and piperidines.

The maleic anhydride adducts may also be reacted with hydroxylic type compounds such as alcohols including glycols and other polyols, polyalkylene glycols, aromatic hydroxyl compounds such as phenols and naphthols; alkylene oxide such as ethylene oxides and propylene oxide.

Examples of such dispersants are the derivatives of alkenyl succinimides disclosed in U.S. Pat. Nos. 3,018,250 (N-dialkyl-aminoalkyl derivatives), 3,024,195 (N-alkylpiperzine derivatives), 3,219,666 (hydroxyalkyl piperazine derivatives), 3,216,936 (alkylene polyamine derivatives), 3,172,892 (ethylene polyamine derivatives), 3,515,669 and 3,779,922 (alkylene polyamine derivatives), 4,803,004 (anylamine derivatives). Particularly preferred hydroxylic compounds are the hindered polyols such as pentaerythritol, dipentaerythritol and trimethylolpropane. Examples of such reaction products are disclosed in U.S. Pat. Nos. 3,708,522 (pentaerythritol ester derivatives post-treated with maleic anhydride), 3,632,510 and 3,522,179 (ester derivatives e.g. acid esters, di-esters, mixed esters, estermetal salts derived from mono- and polyhydric alcohols, phenols, naphthols etc.); 3,579,450, 3,522,179 and 3,381,022 (ester derivatives of alcohols and alkylene oxides e.g. sorbitol and propylene oxide); 4,522,736 (tyrishydroxymethyl amino methane), and 4,803,004 (hindered alcohols).

The reaction products with bifunctional compounds containing two different types of functional group are also preferred, especially those containing both amino and hydroxyl functionality. Reaction products of this type are described, for example, in U.S. Pat. Nos. 4,016,092 and 4,097,389 (reaction with tris(hydroxymethyl) aminomethane), 4,698,169 (alkanolamines) and 4,652,387 (aminoalcohols).

More than one type of compound may also be reacted with the maleic anhydride adducts, for example, an amine and an alcohol or an amine and an alkanolamine. Reaction products of this kind are disclosed, for instance, in U.S. Pat. Nos. 4,698,169 and 4,803,004 (arylamines and alkanolamines or hindered alcohols), 4,522,736 (aromatic amines or phenols and alkarolamines or aminomethanes), 4,652,387 (arylamines and aminoalcohols).

These reaction products of the maleic anhydride adducts with various active hydrogen containing compounds may themselves be subjected to further reaction with other compounds to create additional or different functional groups in the reaction products. For example, esters formed by reaction of the maleic anhydride adducts with polyols such as pentaerythritol may be esterified further e.g. with carboxylic acids, anhydrides, acyl halides or anhydrides to introduce different ester groups, or with inorganic compounds e.g. acids such as boric acid, phosphoric acid, sulfonic acid or substituted acids of these types, to produce borated, phosphorylated or sulfonated derivatives.

Examples of such esterified products are disclosed in U.S. Pat. Nos. 4,016,092, 4,097,389, and 4,652,387. As described there, the initial reaction product between the maleic anhydride adduct and the active hydrogen compound may be reacted with an appropriate amount of the initial reaction product with alkyl borates, boric acid, a dialkyl phosphonate or a diaryl phosphonate to produce the final borated or phosphonate derivatives. Alternative borating agents which may be used are disclosed in U.S. Pat. No. 4,652,387 and include metaboric acid, alkylmetaboraten, alkyl boroxines, boroxine boroxides.

The maleic anhydride adducts produced from the present olefin oligomers may be converted to similar materials to those described above, with the olefin oligomer group replacing the long chain alkenyl groups of the known derivatives. Reference is made to the patents identified above for details of such derivatives as well as of their manner of preparation.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A lubricant additive composition comprising the reaction product of an amine with an adduct of an olefinic oligomer and maleic anhydride, the olefinic oligomer having a branch ratio of less than 0.19, a weight average molecular weight of 300 to 45,000, a number average molecular weight of 300 to 18,000 and a molecular weight distribution from 1 to 5 and a pour point below $-15°$ C., which is the product of the oligomerization of a $C_6$ to $C_{20}$ alpha-olefin feedstock, or mixtures thereof, under oligomerization conditions in contact with a catalyst comprising chromium oxide reduced with carbon monoxide on a porous support.

2. The composition of claim 1 in which the oligomerization of the olefin is carried out at a temperature between 90° C. and 250° C.

3. The composition of claim 1 in which the alpha-olefin is 1-decene.

4. The composition of claim 1 in which the adduct of the oligomer and the maleic anhydride has the structure:

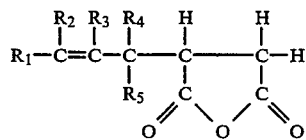

where $R_1$, $R_2$, $R_3$, $R_4$ and $R_5$ are hydrogen, alkyl or alkenyl and at least 17 carbon atoms in total.

5. The composition of claim 1 in which the reaction product comprises the reaction product of the adduct and tetraethylene pentamine.

6. The composition of claim 5 in which the reaction product has the structure:

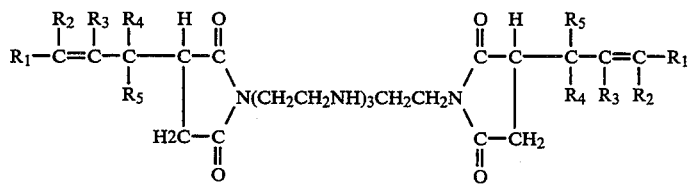

where $R_1$, $R_2$, $R_3$, $R_4$ and $R_5$ are hydrogen, alkyl or alkenyl and the total number of carbon atoms in all R groups is at least 17.

7. In a process for the production of an alkenylsuccinimide derivative of an adduct of maleic anhydride and an olefin oligomer comprising the oligomerization product of a $C_6$ to $C_{20}$ alpha-olefin feed, by reacting the adduct with an amine, the improvement comprising, the use of an olefinic oligomer produced under oligomerization conditions in contact with a catalyst comprising a reduced valence state chromium oxide catalyst on a porous support produced by the carbon monoxide reduction of chromium oxide on a porous support at a temperature of from 250° to 450° C., the olefinic oligomer having a branch ratio of less than 0.19, a weight average molecular weight of 300 to 45,000, a number average molecular weight of 300 to 18,000 and a molecular weight distribution from 1 to 5 and a pour point below $-15°$ C.

8. The process of claim 7 in which the amine comprises a polyamine.

9. The process of claim 8 in which the polyamine is reacted with the adduct to form an alkenyl bis-succinimide.

10. The process of claim 9 in which the alkenyl bis-succinimide has the structure

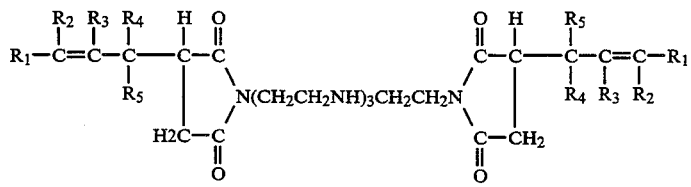

where $R_1$, $R_2$, $R_3$, $R_4$ and $R_5$ are hydrogen, alkyl or alkenyl and the total number of carbon atoms in all R groups is at least 17.

11. The process of claim 7 in which the amine has amine and hydroxyl functionality.

* * * * *

UNITED STATES PATENT AND TRADEMARK OFFICE
CERTIFICATE OF CORRECTION

PATENT NO. : 5,384,055
DATED : January 24, 1995
INVENTOR(S) : Henry Ashjian

It is certified that error appears in the above-indentified patent and that said Letters Patent is hereby corrected as shown below:  Item [63]

Title page, under "Related U.S. Application Data", delete "Ser. No. 342,179, and insert --Ser. No. 342,779--.

Column 1, line 9, delete "07/342,179" and insert --07/342,779--.

Signed and Sealed this

Twenty-sixth Day of September, 1995

Attest:

BRUCE LEHMAN

*Attesting Officer*          *Commissioner of Patents and Trademarks*